US010709656B2

United States Patent
Pi et al.

(10) Patent No.: US 10,709,656 B2
(45) Date of Patent: Jul. 14, 2020

(54) EMULSION COSMETIC COMPOSITION CONTAINING CERAMIDE AND METHOD FOR PREPARING SAME

(71) Applicant: AMOREPACIFIC CORPORATION, Seoul (KR)

(72) Inventors: Bong Soo Pi, Yongin-si (KR); Jin Nam, Yongin-si (KR); Youngsun Kim, Yongin-si (KR); Yu Jin Jin, Yongin-si (KR); Soon Ae An, Yongin-si (KR); Byungyoung Kang, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/988,504

(22) Filed: May 24, 2018

(65) Prior Publication Data

US 2018/0289607 A1 Oct. 11, 2018

Related U.S. Application Data

(63) Continuation-in-part of application No. PCT/KR2016/013607, filed on Nov. 24, 2016.

(30) Foreign Application Priority Data

Nov. 27, 2015 (KR) .................. 10-2015-0167353

(51) Int. Cl.
| | |
|---|---|
| A61K 8/68 | (2006.01) |
| A61Q 19/00 | (2006.01) |
| A61K 8/893 | (2006.01) |
| A61K 8/39 | (2006.01) |
| A61K 8/81 | (2006.01) |
| A61K 8/02 | (2006.01) |
| A61K 8/06 | (2006.01) |
| A61K 8/91 | (2006.01) |

(52) U.S. Cl.
CPC .............. *A61K 8/68* (2013.01); *A61K 8/025* (2013.01); *A61K 8/062* (2013.01); *A61K 8/39* (2013.01); *A61K 8/8158* (2013.01); *A61K 8/893* (2013.01); *A61K 8/91* (2013.01); *A61Q 19/00* (2013.01); *A61K 2800/412* (2013.01); *A61K 2800/54* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 8,241,651 B2 | 8/2012 | Lahann | |
| 2007/0065392 A1 | 3/2007 | Simonnet | |
| 2011/0076311 A1* | 3/2011 | Serizawa | A61K 8/06 424/401 |
| 2011/0112045 A1* | 5/2011 | Wakamatsu | A61K 8/342 514/47 |
| 2013/0047891 A1* | 2/2013 | Takei | C09D 5/165 106/287.11 |
| 2014/0134255 A1 | 5/2014 | Saito et al. | |
| 2014/0220139 A1* | 8/2014 | Park | A61K 9/0014 424/489 |

FOREIGN PATENT DOCUMENTS

| | | |
|---|---|---|
| KR | 1020050053922 A | 6/2005 |
| KR | 1020130030093 A | 3/2013 |
| KR | 101299148 B1 | 8/2013 |
| KR | 1020130103654 A | 9/2013 |
| KR | 1020140016302 A | 2/2014 |
| KR | 1020140063627 A | 5/2014 |
| KR | 1020140073211 A | 6/2014 |
| KR | 1020140091556 A | 7/2014 |
| WO | 2005053633 A1 | 6/2005 |
| WO | 2008058297 A2 | 5/2008 |
| WO | WO2008058297 * | 5/2008 |
| WO | 2012126115 A1 | 9/2012 |
| WO | 2013074931 A1 | 5/2013 |
| WO | WO2014174495 * | 10/2014 |

OTHER PUBLICATIONS

International Search report for PCT/KR2016/03607, dated Mar. 6, 2017 (6 pages with translation).

* cited by examiner

*Primary Examiner* — Robert A Wax
*Assistant Examiner* — Randeep Singh
(74) *Attorney, Agent, or Firm* — Cantor Colburn LLP

(57) ABSTRACT

The present specification relates to an oil-in-water type emulsion cosmetic composition containing an amphiphilic anisotropic powder and ceramide, wherein the amphiphilic anisotropic powder contains a first polymer spheroid which is hydrophilic and a second polymer spheroid which is hydrophobic, wherein the first polymer spheroid and the second polymer spheroid bind by at least partially penetrating the other polymer spheroid, wherein the first polymer spheroid has a core-shell structure, wherein the shell contains a functional group, and wherein the ceramide contains oil phase ceramide included in oil phase and ceramide particles included in water phase.

18 Claims, 2 Drawing Sheets

Right after preparation        After 4 weeks

<Right after preparation>        <After 4 weeks>

EMULSION COSMETIC COMPOSITION CONTAINING CERAMIDE AND METHOD FOR PREPARING SAME

CROSS-REFERENCE TO RELATED APPLICATION

This application is a continuation-in part of PCT/KR2016/013607, filed Nov. 24, 2016, which claims the benefit of KR 10-2015-0167353, both of which are incorporated by reference herein in their entirety.

TECHNICAL FIELD

The present disclosure relates to an emulsion type cosmetic composition including a ceramide and a method for preparing the same.

BACKGROUND ART

Intercellular lipids give a physicochemical barrier effect to the skin. Intercellular lipids mainly include ceramides, fatty acids, cholesterols, cholesterol esters, or the like, and the proportion of ceramides reaches about 40-60%. Ceramides play a very important role in forming a lipid structure and providing a barrier function. Ceramides have characteristics which are difficult to be handled in a cosmetic formulation due to the Wan der Waals attraction between non-polar tails and intermolecular hydrogen bonding occurring in the amino-carbonyl groups and hydroxyl groups of polar head groups. Pseudo-ceramides also have unique thermal behaviors due to their geometrical structures and hydrogen bonding of the head groups, and thus have a difficulty in designing a formulation and controlling a manufacturing process.

Spherical microparticles including polymers have a size and shape controllable depending on preparation methods thereof, and thus have high applicability. For example, there is provided Pickering emulsion which uses spherical microparticles to form stabilized macroemulsion particles. The contact angle ($\theta$) between an aqueous phase and an oil phase varies with hydrophilicity/hydrophobicity of spherical particles. When a contact angle is larger than 90°, O/W emulsion particles are formed. Meanwhile, when a contact angle is smaller than 90°, W/O emulsion particles are formed.

In addition, some attempts have been made to impart amphiphilic property (i.e. both hydrophilic property and hydrophobic property) to spherical microparticles so that novel anisotropic powder may be obtained. This may be exemplified by Janus spherical particles. However, such spherical particles have a limitation in chemical anisotropy due to their morphological limitation. In other words, although the particles are morphologically anisotropic, they may be hydrophobic or hydrophilic as a whole, and thus have limited chemical anisotropy.

Therefore, some attempts have been made to obtain surface active anisotropic powder by controlling a geometrical shape and imparting chemical anisotropy. However, no method for mass production of amphiphilic anisotropic powder has been developed to date, although such amphiphilic anisotropic powder shows high applicability. Moreover, it is difficult to produce amphiphilic anisotropic powder uniformly in a large amount in an industrial scale, leading to a failure in practical application.

DISCLOSURE

Technical Problem

A technical problem to be solved by the present disclosure is to provide a stable emulsion type cosmetic composition including a ceramide.

Another technical problem to be solved by the present disclosure is to provide an emulsion type cosmetic composition which has excellent skin safety.

Still another technical problem to be solved by the present disclosure is to provide an emulsion type cosmetic composition which retains a ceramide stably inside of macroemulsion particles, has an outer-phase ceramide forming stable crystals surrounded with amphiphilic anisotropic powder, includes ceramide particles dispersed homogeneously therein without coalescence of particles, and shows a soft feeling of use without a feeling of irritation and excellent formulation and emulsion stability.

Still another technical problem to be solved by the present disclosure is to provide an emulsion type cosmetic composition which includes ceramide particles dispersed homogeneously therein without coalescence of ceramide particles even in the case of a high content of ceramide, and has excellent formulation and emulsion stability.

Still another technical problem to be solved by the present disclosure is to provide an emulsion type cosmetic composition which provides a stable formulation without using an excessive amount of thickener.

Still another technical problem to be solved by the present disclosure is to provide an emulsion type cosmetic composition which prevents skin irritation by avoiding the use of an excessive amount of thickener, dispersant, surfactant, or the like.

Still another technical problem to be solved by the present disclosure is to provide an emulsion type cosmetic composition which shows a unique feeling of use and a moisturizing effect by virtue of a burst of emulsion particles.

Yet another technical problem to be solved by the present disclosure is to provide an emulsion type cosmetic composition which shows rapid absorbability and provides a soft feeling of use through low viscosity and high spreadability.

Technical Solution

In one general aspect, there is provided an oil-in-water type emulsion cosmetic composition including amphiphilic anisotropic powder and a ceramide, wherein the amphiphilic anisotropic powder includes a first hydrophilic polymer spheroid and a second hydrophobic polymer spheroid, the first polymer spheroid and the second polymer spheroid are bound to each other with a structure in which one polymer spheroid at least partially penetrates into the other polymer spheroid, the first polymer spheroid has a core-shell structure, the shell has a functional group, and the ceramide includes an oil-phase ceramide contained in an oil phase and ceramide particles contained in an aqueous phase.

Advantageous Effects

In one aspect, the present disclosure provides a stable emulsion type cosmetic composition including a ceramide.

In another aspect, the present disclosure provides an emulsion type cosmetic composition which has excellent skin safety.

In still another aspect, the present disclosure provides an emulsion type cosmetic composition which retains a ceramide stably inside of macroemulsion particles, has an outer-phase ceramide forming stable crystals surrounded with amphiphilic anisotropic powder, includes ceramide particles dispersed homogeneously therein without coalescence of particles, and shows a soft feeling of use without a feeling of irritation and excellent formulation and emulsion stability.

In still another aspect, the present disclosure provides an emulsion type cosmetic composition which includes ceramide particles dispersed homogeneously therein without coalescence of ceramide particles even in the case of a high content of ceramide, and has excellent formulation and emulsion stability.

In still another aspect, the present disclosure provides an emulsion type cosmetic composition which provides a stable formulation without using an excessive amount of thickener.

In still another aspect, the present disclosure provides an emulsion type cosmetic composition which prevents skin irritation by avoiding the use of an excessive amount of thickener, dispersant, surfactant, or the like.

In still another aspect, the present disclosure provides an emulsion type cosmetic composition which shows a unique feeling of use and a moisturizing effect by virtue of a burst emulsion particles.

In yet another aspect, the present disclosure provides an emulsion type cosmetic composition which shows rapid absorbability and provides a soft feeling of use through low viscosity and high spreadability.

BEST MODE

Figure 1:
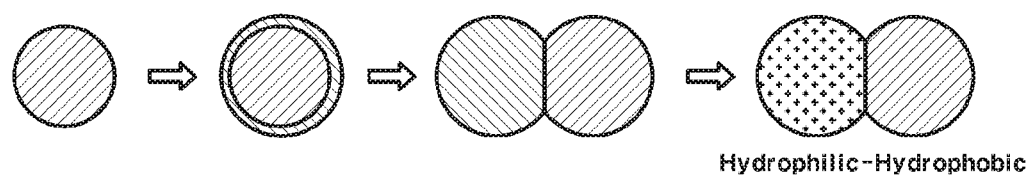
FIG. 1 is a schematic view illustrating the formation of amphiphilic anisotropic powder according to an embodiment of the present disclosure.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these embodiments are provided so that this disclosure will be thorough and complete, and will fully convey the scope of the present disclosure to those skilled in the art. In the drawings, the shape, size and regions, and the like, of the drawing may be exaggerated for clarity. In addition, although a part of constitutional elements is shown for convenience of description, the remaining part may be understood with ease by those skilled in the art. Further, it will be understood by those skilled in the art that various changes in form and details may be made thereto without departing from the scope of this disclosure as defined by the appended claims.

As used herein, "substituted" means that at least one hydrogen atom of the functional group described herein is substituted with a halogen atom (F, Cl, Br or I), hydroxyl group, nitro group, imino group (=NH, =NR, wherein R is a C1-C10 alkyl group), amidino group, hydrazine or hydrazone group, carboxyl group, substituted or non-substituted C1-C20 alkyl group, substituted or non-substituted C3-C30 heteroaryl group, or substituted or non-substituted C2-C30 heterocycloalkyl group, unless otherwise stated.

As used herein, "(meth)acryl" means acryl and/or methacryl.

As used herein, the particle size of amphiphilic anisotropic powder is measured as the maximum length that is the maximum length of the powder particles. As used herein, the particle size range of amphiphilic anisotropic powder means that at least 95% of the amphiphilic anisotropic powder present in a composition belongs to the corresponding range.

As used herein, the average particle diameter of emulsion particles means the average of diameter of each particle. As used herein, the average particle diameter range of emulsion particles means that at least 95% of the emulsion particles present in a composition belongs to the corresponding range.

As used herein, the average particle diameter of ceramide particles means the volumetric average particle diameter obtained by calculating the volumetric average based on the particle size distribution determined by the known methods for determining a particle size distribution, such as observation of electron microscopic images, laser diffraction, or the like.

In one aspect, there is provided an emulsion type cosmetic composition including a ceramide and amphiphilic anisotropic powder. The composition including a ceramide may provide a cosmetic composition having excellent skin absorbability and an excellent moisturizing effect.

According to an embodiment, the emulsion type cosmetic composition may be an oil-in-water (O/W) type composition.

According to another embodiment, the ceramide may be used in an amount of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1.0 wt % or more, 1.1 wt % or more, 1.2 wt % or more, 1.3 wt % or more, 1.4 wt % or more, 1.5 wt % or more, 1.6 wt % or more, 1.7 wt % or more, 1.8 wt % or more, 1.9 wt % or more, 2.0 wt % or more, 2.1 wt % or more, 2.2 wt % or more, 2.3 wt % or more, 2.4 wt % or more, 2.5 wt % or more, 2.6 wt % or more, 2.7 wt % or more, 2.8 wt % or more, 2.9 wt % or more, 3 wt % or more, 3.1 wt % or more, 3.2 wt % or more, 3.3 wt % or more, 3.4 wt % or more, 3.5 wt % or more, 3.6 wt % or more, 3.7 wt % or more, 3.8 wt % or more, 3.9 wt % or more, or 4 wt % or more; and 30 wt % or less, 29.5 wt % or less, 29 wt % or less, 28.5 wt % or less, 28 wt % or less, 27.5 wt % or less, 27 wt % or less, 26.5 wt % or less, 26 wt % or less, 25.5 wt % or less, 25 wt % or less, 24.5 wt % or less, 24 wt % or less, 23.5 wt % or less, 23 wt % or less, 22.5 wt % or less, 22 wt % or less, 21.5 wt % or less, 21 wt % or less, 20.5 wt % or less, 20 wt % or less, 19.5 wt % or less, 19 wt % or less, 18.5 wt % or less, 18 wt % or less, 17.5 wt % or less, 17 wt % or less, 16.5 wt % or less, 16 wt % or less, 15.5 wt % or less, 15 wt % or less, 14.5 wt % or less, 14 wt % or less, 13.5 wt % or less, 13 wt % or less, 12.5 wt % or less, 12 wt % or less, 11.5 wt % or less, 11 wt % or less, 10.5 wt % or less, 10 wt % or less, 9.5 wt % or less, 9 wt % or less, 8.5 wt % or less, or 8 wt % or less, based on the total weight of the composition. For example, the ceramide may be used in an amount of 0.1 wt %-30 wt %, 0.5 wt %-20 wt %, 0.5 wt %-10 wt %, 1 wt %-12 wt %, 2 wt %-10 wt %, or 4 wt %-8 wt %, based on the total weight of the composition. It is possible to provide excellent formulation stability and to enhance a skin moisturizing effect and absorbability within the above-defined range.

According to an embodiment of the present disclosure, the ceramide may be contained partially or totally in an oil phase. The oil-phase ceramide contained in an oil phase is present inside of emulsion particles forming a firm interface layer to form a stable emulsion formulation, and may provide a unique feeling of use by bursting of macroemulsion particles causing ejection of an inner phase upon the skin application.

According to another embodiment, the ceramide may be contained partially or totally in an aqueous phase. The ceramide contained in an aqueous phase is surrounded with amphiphilic anisotropic powder to form a crystalline shape, which is referred to as a ceramide particle herein. The ceramide particles are present in the aqueous phase stably without coalescence of particles. In addition, ceramide particles formed by mixing with anisotropic powder may provide a soft feeling of use without a feeling of irritation upon the skin application.

The ceramide particles may be present in an amount of 50 wt % or more, 51 wt % or more, 52 wt % or more, 53 wt % or more, 54 wt % or more, 55 wt % or more, 56 wt % or more, 57 wt % or more, 58 wt % or more, 59 wt % or more, 60 wt % or more, 61 wt % or more, 62 wt % or more, 63 wt % or more, 64 wt % or more, 65 wt % or more, 66 wt % or more, 67 wt % or more, 68 wt % or more, 69 wt % or more, 70 wt % or more, 71 wt % or more, 72 wt % or more, 73 wt % or more, 74 wt % or more, 75 wt % or more, 76 wt % or more, 77 wt % or more, 78 wt % or more, 79 wt % or more, 80 wt % or more, 81 wt % or more, 82 wt % or more, 83 wt % or more, 84 wt % or more, 85 wt % or more, 86 wt % or more, 87 wt % or more, 88 wt % or more, 89 wt % or more, or 90 wt % or more; and 95 wt % or less, 94 wt % or less, 93 wt % or less, 92 wt % or less, 91 wt % or less, 90 wt % or less, 89 wt % or less, 88 wt % or less, 87 wt % or less, 86 wt % or less, 85 wt % or less, 84 wt % or less, 83 wt % or less, 82 wt % or less, 81 wt % or less, 80 wt % or less, 79 wt % or less, 78 wt % or less, 77 wt % or less, 76 wt % or less, 75 wt % or less, 74 wt % or less, 73 wt % or less, 72 wt % or less, 71 wt % or less, 70 wt % or less, 69 wt % or less, 68 wt % or less, 67 wt % or less, 66 wt % or less, 65 wt % or less, 64 wt % or less, 63 wt % or less, 62 wt % or less, 61 wt % or less, 60 wt % or less, 59 wt % or less, 58 wt % or less, 57 wt % or less, 56 wt % or less, or 55 wt % or less, particularly in an amount of 50 wt %-95 wt %, based on the total weight of ceramide including the oil-phase ceramide and ceramide particles. It is possible to provide a composition with excellent absorbability and a soft feeling of use within the above-defined range.

The ceramide particles may have an average particle diameter of 5-200 μm. It is possible to provide a soft feeling of use without a feeling of irritation within the above-defined range.

According to another embodiment, the ceramide may be at least one of natural ceramides and pseudo-ceramides.

For example, According to still another embodiment, the pseudo-ceramide may be at least one selected from the compounds represented by the following Chemical Formulae 1-5, but is not limited thereto:

[Chemical Formula 1]

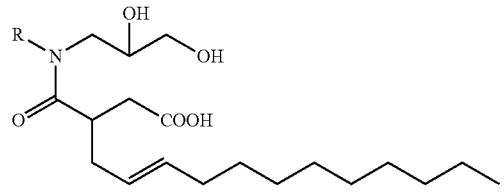

(wherein R is a C9-C21 saturated or unsaturated aliphatic chain.)

[Chemical Formula 2]

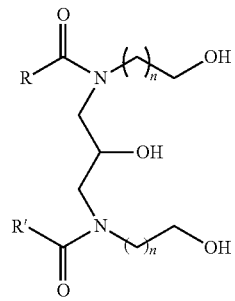

(wherein n is 1 or 2; and each of R and R' is a C9-C21 saturated or unsaturated aliphatic chain.)

[Chemical Formula 3]

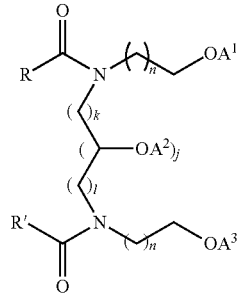

[wherein m and n are the same or different and each represents an integer of 1-3;

k and l are the same or different and each represents 1 or 2;

j is 0 or 1;

R and R' are the same or different and each represents a C1-C31 linear or branched saturated or unsaturated alkyl group containing a hydroxyl group or not;

$A^1$, $A^2$ and $A^3$ are the same or different and each represents H or any one of the substituents represented by the following structures, with the proviso that $A^1$, $A^2$ and $A^3$ cannot represent H at the same time:

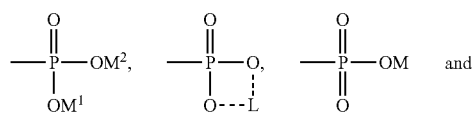

-continued

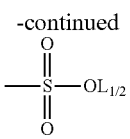

(wherein each of M, M¹ and M² is selected from the group consisting of alkali metals, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal).]

[Chemical formula 4]

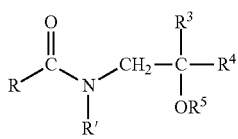

[wherein R and R' are the same or different and each represents a C10-C32 linear or branched saturated or unsaturated alkyl group containing a hydroxyl group or not;

$R^3$ and $R^4$ are the same or different and each represents H or a C1-C4 alkyl group or hydroxyalkyl group; and $R^5$ is -A or —$CH_2CH_2OA$, wherein A is any one of the substituents represented by the following structures:

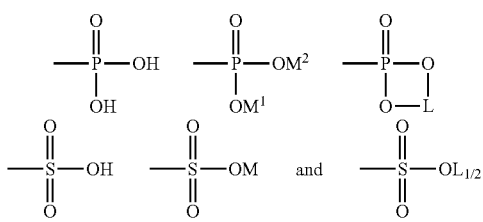

(wherein each of M, M¹ and M² is selected from the group consisting of alkali metals, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal).]

[Chemical formula 5]

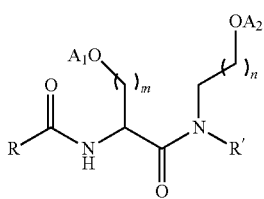

[wherein m and n are the same or different and each represents an integer of 1-4; R and R' are the same or different and each represents a C1-C31 linear or branched saturated or unsaturated alkyl group containing a hydroxyl group or not; and $A_1$ and $A_2$ are the same or different and each represents H or any one of the substituents represented by the following structures:

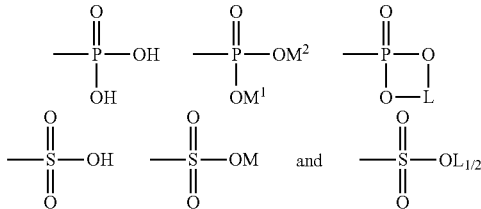

(wherein M, M¹ and M² is selected from the group consisting of alkali metals, lysine, arginine, histidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal).]

According to still another embodiment, the amphiphilic anisotropic powder includes a first hydrophilic polymer spheroid and a second hydrophobic polymer spheroid, wherein the first polymer spheroid and the second polymer spheroid are bound to each other with a structure in which one polymer spheroid at least partially penetrates into the other polymer spheroid, the first polymer spheroid has a core-shell structure, and the shell has a functional group.

As used herein, a spheroid means a single body formed of polymers. For example, it may have a spherical, globoidal or oval shape and a micro-scale or nano-scale long axis length based on the largest length in the section of the body.

According to an embodiment, the second polymer spheroid and the core of the first polymer spheroid may include vinyl polymers, and the shell of the first polymer spheroid may include a copolymer of a vinyl monomer with a functional group-containing monomer.

According to another embodiment, the vinyl polymer may include a vinyl aromatic polymer, particularly polystyrene.

According to still another embodiment, the vinyl monomer may include a vinyl aromatic monomer. For example, the vinyl monomer may be substituted or non-substituted styrene.

According to still another embodiment, the functional group may be siloxane.

According to still another embodiment, the functional group-containing monomer may be a siloxane-containing (meth)acrylate, particularly at least one selected from the group consisting of 3-(trimethoxysilyl)propyl acrylate, 3-(trimethoxysilyl)propyl methacrylate, vinyltriethoxysilane and vinyltrimethoxysilane, or a combination thereof.

According to still another embodiment, the shell of the polymer spheroid may further have a hydrophilic functional group introduced thereto.

According to still another embodiment, the hydrophilic functional group may be a negatively charged or positively charged functional group or polyethylene glycol (PEG)-based functional group and may include at least one selected from the group consisting of a carboxylate group, sulfone group, phosphate group, amino group, alkoxy group, ester group, acetate group, polyethylene glycol group and hydroxyl group.

According to still another embodiment, the shell of the first polymer spheroid may further have a saccharide-containing functional group introduced thereto.

According to still another embodiment, the saccharide-containing functional group may be derived from at least one selected from the group consisting of N—{N-(3-triethoxysilylpropyl)aminoethyl}gluconamide, N-(3-triethoxysilylpropyl) gluconamide and N—{N-(3-triethoxysilylpropyl)aminoethyl}-oligo-hyaluronamide.

According to still another embodiment, the amphiphilic anisotropic powder may have a symmetric shape, asymmetric snowman shape or asymmetric reverse snowman shape on the basis of the binding portion where the first polymer spheroid and the second polymer spheroid are bound to each other. The snowman shape refers to the first polymer spheroid and the second polymer spheroid bound to each other and having a different size.

According to still another embodiment, the amphiphilic anisotropic powder may have a particle size of 100-2500 nm. In a variant, the amphiphilic anisotropic powder may have a particle size of 100-1500 nm, 100-500 nm, or 200-300 nm. Particularly, the amphiphilic powder may have a particle size of 100 nm or more, 200 nm or more, 300 nm or more, 400 nm or more, 500 nm or more, 600 nm or more, 700 nm or more, 800 nm or more, 900 nm or more, 1000 nm or more, 1100 nm or more, 1200 nm or more, 1300 nm or more, 1400 nm or more, or 1500 nm or more; and 2500 nm or less, 2400 nm or less, 2300 nm or less, 2200 nm or less, 2100 nm or less, 2000 nm or less, 1900 nm or less, 1800 nm or less, 1700 nm or less, 1600 nm or less, 1500 nm or less, 1400 nm or less, 1300 nm or less, 1200 nm or less, 1100 nm or less, 1000 nm or less, 900 nm or less, 800 nm or less, 700 nm or less, 600 nm or less, 500 nm or less, 400 nm or less, 300 nm or less, or 200 nm or less.

According to still another embodiment, the amphiphilic anisotropic powder may form macroemulsion particles having a size of 2-500 μm. In a variant, the amphiphilic anisotropic powder may form macroemulsion particles having a size of 5-400 μm, 10-350 μm, 30-300 μm, or 50-300 μm. Particularly, the amphiphilic anisotropic powder may form emulsion particles having a size of 2 μm or more, 3 μm or more, 4 μm or more, 5 μm or more, 6 μm or more, 7 μm or more, 8 μm or more, 9 μm or more, 10 μm or more, 11 μm or more, 12 μm or more, 13 μm or more, 14 μm or more, 15 μm or more, 16 μm or more, 17 μm or more, 18 μm or more, 19 μm or more, 20 μm or more, 21 μm or more, 22 μm or more, 23 μm or more, 24 μm or more, 25 μm or more, 26 μm or more, 27 μm or more, 28 μm or more, 29 μm or more, 30 μm or more, 31 μm or more, 32 μm or more, 33 μm or more, 34 μm or more, 35 μm or more, 36 μm or more, 37 μm or more, 38 μm or more, 39 μm or more, 40 μm or more, 41 μm or more, 42 μm or more, 43 μm or more, 44 μm or more, 45 μm or more, 46 μm or more, 47 μm or more, 48 μm or more, 49 μm or more, or 50 μm or more; and 500 μm or less, 490 μm or less, 480 μm or less, 470 μm or less, 460 μm or less, 450 μm or less, 440 μm or less, 430 μm or less, 420 μm or less, 410 μm or less, 400 μm or less, 390 μm or less, 380 μm or less, 370 μm or less, 360 μm or less, 350 μm or less, 340 μm or less, 330 μm or less, 320 μm or less, 310 μm or less, 300 μm or less, 290 μm or less, 280 μm or less, 270 μm or less, 260 μm or less, 250 μm or less, 240 μm or less, 230 μm or less, 220 μm or less, 210 μm or less, 200 μm or less, 190 μm or less, 180 μm or less, 170 μm or less, 160 μm or less, or 150 μm or less.

Since the hydrophobic part and hydrophilic part of the amphiphilic anisotropic powder have different orientability against the interface, it is possible to form macroemulsion particles. It is possible to provide an emulsion formulation having various viscosities, including a formulation having a less viscous soft feeling of use, by virtue of such macroemulsion particles.

While an interface layer formed by a conventional molecular-level surfactant forms a dynamic emulsion phase, the thickness of the interface layer of the emulsion particles formed by the amphiphilic anisotropic powder increases to several hundreds of nanometers and a stabilized interface layer is formed by virtue of the strong binding among the powder particles. Such formation of an interface layer improves emulsion stability. In addition, it is possible to maintain a stable emulsion state, while not being affected by the ceramide. Further, the ceramide which is not precipitated from the inner phase, is not included in the emulsion particles, but is present in the outer phase is surrounded with amphiphilic anisotropic powder to form crystals and to provide stable ceramide particles. Such ceramide particles are dispersed homogeneously in the composition to maintain the composition stably while not affecting the interface layer of emulsion particles.

According to still another embodiment, the amphiphilic anisotropic powder may be present in an amount of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, or 1.0 wt % or more; and 30 wt % or less, 29 wt % or less, 28 wt % or less, 27 wt % or less, 26 wt % or less, 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, or 3 wt % or less, based on the total weight of the composition. For example, the amphiphilic anisotropic powder may be present in an amount of 0.1-10 wt %, based on the total weight of the composition. It is possible to form stable emulsion particles and to form emulsion particles having an adequate size within the above-defined range.

The composition may have a viscosity of 1000 cps or more, 1100 cps or more, 1200 cps or more, 1300 cps or more, 1400 cps or more, 1500 cps or more, 1600 cps or more, 1700 cps or more, 1800 cps or more, 1900 cps or more, 2000 cps or more, 2100 cps or more, 2200 cps or more, 2300 cps or more, 2400 cps or more, or 2500 cps or more; and 30000 cps or less, 29000 cps or less, 28000 cps or less, 27000 cps or less, 26000 cps or less, 25000 cps or less, 24000 cps or less, 23000 cps or less, 22000 cps or less, 21000 cps or less, 20000 cps or less, 19000 cps or less, 18000 cps or less, 17000 cps or less, 16000 cps or less, 15000 cps or less, 14000 cps or less, 13000 cps or less, 12000 cps or less, 11000 cps or less, 10000 cps or less, 8900 cps or less, 8800 cps or less, 8700 cps or less, 8600 cps or less, 8500 cps or less, 8400 cps or less, 8300 cps or less, 8200 cps or less, 8100 cps or less, 8000 cps or less, 7900 cps or less, 7800 cps or less, 7700 cps or less, 7600 cps or less, 7500 cps or less, 7400 cps or less, 7300 cps or less, 7200 cps or less, 7100 cps or less, 7000 cps or less, 6900 cps or less, 6800 cps or less, 6700 cps or less, 6600 cps or less, 6500 cps or less, 6400 cps or less, 6300 cps or less, 6200 cps or less, 6100 cps or less, or 6000 cps or less. For example, the viscosity may be 1000-30000 cps, 1000-20000 cps, 1000-10000 cps, 1500-10000 cps, or 2000-7000 cps. The composition may form macroemulsion particles containing an oil-phase ceramide and having a firm emulsion interface. In addition, single amphiphilic anisotropic powder that does not form emulsion particles is also present in the outer phase to allow the ceramide particles present in the outer phase to be dispersed homogeneously without precipitation or coalescence. Further, the formulation may have excellent emulsion stability.

Since the composition maintains the stability of an emulsion formulation without using an additional thickener or wax, even when a high content of ceramide is used, it is possible to provide a composition with the above-mentioned broad range of viscosities. Even when a high content of ceramide is used, it is possible to provide a low-viscosity composition having a viscosity of 8000 cps or less, 7000 cps or less, or 4000-7000 cps. It is possible to provide a flowable soft formulation and to realize a non-sticky fresh feeling of use within the above-defined range.

The cosmetic composition according to an embodiment of the present disclosure may be obtained by the method which includes preparing the amphiphilic anisotropic powder, and emulsifying an oil phase part and an aqueous phase part by using the amphiphilic anisotropic powder.

According to an embodiment, the amphiphilic anisotropic powder may be obtained by the method, including: polymerizing a first monomer to obtain a core of a first polymer spheroid; coating the core of the first polymer spheroid to obtain a first polymer spheroid having a core-shell structure; and reacting the first polymer spheroid having a core-shell structure with a first monomer to obtain amphiphilic anisotropic powder in which a second polymer spheroid is formed.

FIG. 1 is a schematic view illustrating formation of the amphiphilic anisotropic powder according to an embodiment of the present disclosure. It is possible to form a second polymer spheroid by allowing the core of the first polymer spheroid to penetrate through the shell of the first polymer spheroid and to grow toward the exterior by using the above-mentioned method.

According to another embodiment, the method for preparing amphiphilic anisotropic powder may include: (1) agitating a first monomer and a polymerization initiator to form a core of a first polymer spheroid; (2) agitating the formed core of a first polymer spheroid with a first monomer, a polymerization initiator and a functional group-containing monomer to form a first polymer spheroid having a coated core-shell structure; and (3) agitating the formed first polymer spheroid having a core-shell structure with a second monomer and a polymerization initiator to obtain anisotropic powder in which a second polymer spheroid is formed.

In steps (1), (2) and (3), the agitation may be rotary agitation. Since homogeneous mechanical mixing is required together with chemical modification in order to produce uniform particles, rotary agitation is preferred. The rotary agitation may be carried out in a cylindrical reactor but is not limited thereto.

Herein, the internal design of the reactor significantly affects powder formation. The size and position of the baffles of the cylindrical reactor and the distance from an impeller have a significant effect upon the uniformity of the particles to be produced. Preferably, the interval between the internal baffle and the blade of an impeller is minimized to make convection flow and intensity thereof uniform, the powdery reaction mixture is introduced to a level lower than the baffle length, and the impeller is maintained at a high rotation speed. The rotation speed may be 200 rpm or higher, and the ratio of the diameter to the height of the reactor may be 1-3:1-5. Particularly, the reactor may have a diameter of 10-30 cm and a height of 10-50 cm. The reactor may have a size variable in proportion to the reaction capacity. In addition, the cylindrical reactor may be made of ceramics, glass or the like. The agitation is carried out preferably at a temperature of 50-90° C.

Simple mixing in a cylindrical rotary reactor allows production of uniform particles, requires low energy consumption and provides maximized reaction efficiency, and thus is amenable to mass production. The conventional tumbling method including rotation of a reactor itself causes inclination of the whole part of the reactor with a certain angle and rotation at a high speed, and thus requires high energy consumption and limits the reactor size. Due to such limitation in reactor size, the output is limited to a small amount of approximately several tens of milligrams to several grams. Thus, the conventional tumbling method is not suitable for mass production.

According to an embodiment, the first monomer and the second monomer may be the same or different, and particularly may be a vinyl monomer. In addition, the first monomer added in step (2) may be the same as the first monomer used in step (1) and the polymerization initiator used in each step may be the same or different.

According to another embodiment, the vinyl monomer may be a vinyl aromatic monomer. The vinyl aromatic monomer may be substituted or non-substituted styrene.

According to still another embodiment, the polymerization initiator may be a radical polymerization initiator. Particularly, the polymerization initiator may be a peroxide-based or azo-based initiator, or a combination thereof. In addition, ammonium persulfate, sodium persulfate or potassium persulfate may be used.

According to still another embodiment, in step (1), the first monomer and the polymerization initiator may be mixed at a weight ratio of 100-1000:1. In a variant, the first monomer and the polymerization initiator may be mixed at a weight ratio of 100-750:1, 100-500:1, or 100-250:1.

In a variant, in step (1), a stabilizer is added together with the first monomer and the polymerization initiator in such a manner that the first monomer, the polymerization initiator and the stabilizer may be mixed at a weight ratio of 100-1000:1:0.001-5. The size and shape of the powder is determined by controlling the size of the first polymer spheroid in step (1), and the size of the first polymer spheroid may be controlled by the ratio of the first monomer, the polymerization initiator and the stabilizer. In addition, it is possible to increase the uniformity of anisotropic powder in its size and shape by mixing the first monomer, the polymerization initiator and the stabilizer within the above-defined ratio.

According to an embodiment, the stabilizer may be an ionic vinyl monomer, and particularly sodium 4-vinylbenzene sulfonate may be used. The stabilizer prevents swelling of the particles, and imparts positive or negative charges to the powder surface, thereby preventing coalescence (binding) of the particles electrostatically.

When the amphiphilic anisotropic powder has a size of 200-250 nm, it may be obtained from the first polymer spheroid including the first monomer, the polymerization initiator and the stabilizer at a ratio of 80-135:1:2-4, particularly 95-120:1:2-4.

In addition, when the amphiphilic anisotropic powder has a size of 400-450 nm, it may be obtained from the first polymer spheroid including the first monomer, the polymerization initiator and the stabilizer at a ratio of 225-240:1:1-3, particularly 230-235:1:1-3.

Further, when the amphiphilic anisotropic powder has a size of 1100-2500 nm, it may be obtained from the first polymer spheroid prepared by reacting the first monomer, the polymerization initiator and the stabilizer at a ratio of 110-130:1:0, particularly 115-125:1:0.

In addition, amphiphilic anisotropic powder having an asymmetric snowman shape may be obtained from the first polymer spheroid prepared by reacting the first monomer, the polymerization initiator and the stabilizer at a ratio of 100-140:1:8-12, particularly 110-130:1:9-11.

Further, amphiphilic anisotropic powder having an asymmetric reverse snowman shape may be obtained from the first polymer spheroid prepared by reacting the first monomer, the polymerization initiator and the stabilizer at a ratio of 100-140:1:1-5, particularly 110-130:1:2-4.

According to still another embodiment, the functional group-containing monomer in step (2) may be a siloxane-containing (meth)acrylate, such as 3-(trimethoxysilyl)propyl acrylate, 3-(trimethoxysilyl)propyl methacrylate, vinyl triethoxysilane, vinyl trimethoxysilane or a combination thereof.

According to still another embodiment, in step (2), the first monomer, the polymerization initiator and the functional group-containing compound may be mixed at a weight ratio of 30-100:0.2-1.0:1-20. In a variant, the first monomer, the polymerization initiator and the functional group-containing compound may be mixed at a weight ratio of 150-300:1:6-40. It is possible to control the coating degree according to the reaction ratio, and then the coating degree determines the shape of amphiphilic anisotropic powder. When the first monomer, the polymerization initiator and the functional group-containing compound are used within the above-defined ratio, the coating thickness is increased by about 10-30%, particularly approximately 20%, based on the initial thickness. In this case, formation of powder proceeds smoothly without problems, such as a failure in formation of powder caused by excessively thick coating or multi-directional formation of powder caused by excessively thin coating. In addition, it is possible to increase the uniformity of anisotropic powder within the above weight ratio.

In step (3), the core of the first polymer spheroid penetrates through the shell from one direction of the first polymer spheroid having a core-shell structure and protrudes out from the shell. Then, the protrusion may be grown by the polymer of the second monomer to form a shape of anisotropic powder.

According to still another embodiment, in step (3), the second monomer and the polymerization initiator may be mixed at a weight ratio of 150-250:1. In a variant, the second monomer and the polymerization initiator may be mixed at a weight ratio of 160-250:1, 170-250:1, 180-250:1, 190-250:1, 200-250:1, 210-250:1, 220-250: 1, 230-250:1, or 240-250:1.

In a variant, in step (3), a stabilizer may be added together with the second monomer and the polymerization initiator in such a manner that the second monomer, the polymerization initiator and the stabilizer may be mixed at a weight ratio of 150-250:1:0.001-5. Particular examples of the stabilizer are the same as described above. It is possible to increase the uniformity of anisotropic powder within the above weight ratio.

According to still another embodiment, in step (3), the second monomer may be mixed in an amount of 40-300 parts by weight based on 100 parts by weight of the first polymer spheroid having a core-shell structure. Particularly, when the content of the second monomer is 40-100 parts by weight based on 100 parts by weight of the first polymer spheroid, asymmetric snowman-like powder is obtained. When the content of the second monomer is 100-150 parts by weight or 110-150 parts by weight, symmetric powder is obtained. In addition, when the content of the second monomer is 150-300 parts by weight or 160-300 parts by weight, asymmetric reverse snowman-like powder is obtained. It is possible to increase the uniformity of anisotropic powder within the above weight ratio.

According to still another embodiment, the method for preparing amphiphilic anisotropic powder may further include, after step (3), step (4) of introducing a hydrophilic functional group to the anisotropic powder.

According to still another embodiment, the hydrophilic functional group in step (4) may be introduced by using a silane coupling agent and a reaction modifier, but is not limited thereto.

According to still another embodiment, the silane coupling agent may be at least one selected from the group consisting of N-[(3-(trimethoxysilyl)propyl)ethylenediamine, N-[3-(trimethoxysilyl)propyl]ethylene diammonium chloride, (N-succinyl-3-aminopropyl)trimethoxysilane, 1-[3-(trimethoxysilyl)propyl]urea and 3-[(trimethoxysilyl)propyloxy]-1,2-propanediol. Particularly, the silane coupling agent may be N-[(3-(trimethoxysilyl) propyl)ethylenediamine.

According to still another embodiment, the silane coupling agent may be mixed in an amount of 35-65 parts by weight, particularly 40-60 parts by weight, based on 100 parts by weight of the anisotropic powder obtained from step (3). It is possible to carry out hydrophilization adequately within the above-defined range.

According to still another embodiment, the reaction modifier may be ammonium hydroxide.

According to still another embodiment, the reaction modifier may be mixed in an amount of 85-115 parts by weight, particularly 90-110 parts by weight, based on 100 parts by weight of the anisotropic powder obtained from step (3). It is possible to carry out hydrophilization adequately within the above-defined range.

According to still another embodiment, the method for preparing amphiphilic anisotropic powder may further include step (4) of introducing a saccharide-containing functional group to the anisotropic powder, after step (3).

In step (4), the saccharide-containing functional group may be introduced by using a saccharide-containing silane coupling agent and a reaction modifier, but is not limited thereto.

According to still another embodiment, the saccharide-containing silane coupling agent may be at least one selected from the group consisting of N—{N-(3-triethoxysilylpropyl)aminoethyl}gluconamide, N-(3-triethoxysilylpropyl)gluconamide and N—{N-(3-triethoxysilylpropyl)aminoethyl}-oligo-hyaluronamide.

According to still another embodiment, the reaction modifier may be ammonium hydroxide.

According to still another embodiment, the reaction modifier may be mixed in an amount of 85-115 parts by weight, particularly 90-110 parts by weight, based on 100 parts by weight of the anisotropic powder obtained from step (3). It is possible to introduce the saccharide-containing functional group adequately within the above-defined range.

The method for preparing amphiphilic anisotropic powder disclosed herein uses no crosslinking agent, thereby causing no agglomeration and providing high yield and uniformity. In addition, the method disclosed herein uses a simple agitation process and is more amenable to mass production as compared to a tumbling process. Particularly, the method disclosed herein is advantageous in that it allows production of nano-size particles having a size of 300 nm or less in a large scale of several tens of grams and several tens of kilograms.

According to still another embodiment, the composition according to an embodiment of the present disclosure may form a formulation having a characteristic feeling of use by virtue of a burst of macroemulsion particles, not a conventional viscous/hard formulation. The composition according to an embodiment of the present disclosure allows a ceramide to be dispersed homogeneously therein without using a high content of thickener, and thus prevents stickiness or skin irritation caused by a thickener.

The composition according to an embodiment of the present disclosure undergoes collapse of the formulation with ease upon the application to the skin, thereby providing a feeling of use with smooth spreadability.

The composition according to an embodiment of the present disclosure may prevent skin irritation that may occur due to the addition of a dispersant or an excessive amount of surfactant.

The composition according to an embodiment of the present disclosure shows excellent emulsion stability even though it contains a ceramide, and thus may provide a soft feeling of use as an emulsion composition simultaneously with skin absorbability and a moisturizing effect. Particularly, the composition shows the above-mentioned effects while the stability thereof is not affected even in the presence of a high content of ceramide.

The composition according to an embodiment of the present disclosure may avoid a sticky finishing feeling caused by a surfactant. In addition, it is possible to provide a formulation with a matte and powdery finishing feeling by virtue of the presence of amphiphilic anisotropic powder that does not form emulsion particles.

The composition according to an embodiment of the present disclosure shows emulsion stability with time over a broad range of temperatures, such as a temperature ranging from −15° C. to 60° C., particularly from −10° C. to 55° C.

The composition according to an embodiment of the present disclosure includes macroemulsion particles to provide a soft and silky feeling of use.

The composition according to an embodiment of the present disclosure may be formulated by incorporating a cosmetically or dermatologically acceptable medium or base thereto. Such a formulation includes any formulation suitable for local application, and may be provided in the form of suspension, microemulsion, microcapsules, microgranules or ionic (liposome) and non-ionic vesicular dispersant, or in the form of cream, skin, lotion, powder, ointment, spray or conceal stick. In addition, the composition may be used in the form of foam or an aerosol composition further including a pressurized propellant. Such compositions may be obtained by the methods known to those skilled in the art.

The composition according to an embodiment of the present disclosure may include supplementary ingredients conventionally used in the field of cosmetics or dermatology, such as powder, a fat material, organic solvent, solubilizer, concentrating agent, gelling agent, softening agent, antioxidant, suspending agent, stabilizer, foaming agent, perfuming agent, surfactant, water, ionic or non-ionic emulsifier, filler, metal ion chelator, chelating agent, preservative, vitamin, protector, wetting agent, essential oil, dye, pigment, hydrophilic or oleophilic activating agent, lipid vesicles or any other ingredients conventionally used for cosmetics. Such supplementary ingredients are introduced in an amount used generally in the field of cosmetics or dermatology. The composition according to an embodiment of the present disclosure may further include a skin absorption enhancer to increase the effect of improving skin conditions.

MODES FOR INVENTION

The examples will now be described to illustrate the present disclosure in detail. It will be appreciated by those skilled in the art that the following examples are for illustrative purposes only and not intended to limit the scope of the present disclosure.

Preparation Examples 1-4

Preparation Examples 1-4 are obtained according to the compositions of the following Table 1. The preparation method will be explained hereinafter.

The ingredients used for Preparation Examples 1-4 are shown below.

TABLE 1

| PS (1 L shaking type reaction tank) | | CS | | DB | |
| --- | --- | --- | --- | --- | --- |
| Water | 300 | PS | 300 | CS | 240 |
| MeOH | 40 | Water | 250 | Water | 350 |
| Styrene | 50 | TMSPA | 6 | AIBN | 0.2 |
| KPS | 0.5 | Styrene | 50 | Styrene | 40 |
| SVBS | 1.0 | AIBN | 0.2 | SVBS | 0.35 |

MeOH: Methanol (cosolvent)
KPS: Potassium persulfate (initiator)
SVBS: Sodium vinyl benzene sulfonate (stabilizer)
PS: Polystyrene (polymer beads)
CS: Coated first polymer spheroid having a core-shell structure
DB: amphiphilic anisotropic powder
TMSPA: Trimethoxysilyl propyl acrylate (functional group)
AIBN: Azobisisobutyronitrile (polymerization initiator)

Preparation Example 1. Preparation of Polystyrene (PS) First Polymer Spheroid

First, 50 g of styrene as a monomer, 1.0 g of sodium 4-vinylbenzene sulfonate as a stabilizer and 0.5 g of azobisisobutyronitrile (AIBN) as a polymerization initiator are mixed in an aqueous phase and are allowed to react at 75° C. for 8 hours. The reaction is carried out by agitating the reaction mixture in a cylindrical reactor having a diameter of 11 cm and a height of 17 cm and made of glass under a speed of 200 rpm.

Preparation Example 2. Preparation of Coated First Polymer Spheroid Having Core-Shell (CS) Structure First, 300 g of the polystyrene (PS) first polymer spherical particles obtained as described above are mixed with 50 g of styrene as a monomer, 6 g of 3-(trimethoxysilyl)propyl acrylate (TMSPA) and 0.2 g of azobisisobutyronitrile (AIBN) as a polymerization initiator and the reaction mixture is allowed to react at 75° C. for 8 hours. The reaction is carried out by agitating the reaction mixture in a cylindrical reactor.

Preparation Example 3. Preparation of Amphiphilic Anisotropic Powder (DB)

First, 240 g of the aqueous dispersion of the polystyrene-core shell (PC-CS) dispersion obtained as described above is mixed with 40 g of styrene as a monomer, 0.35 g of sodium 4-vinylbenzene sulfonate as a stabilizer and 0.2 g of azobisisobutyronitrile (AIBN) as a polymerization initiator and the reaction mixture is heated to 75° C. to carry out reaction for 8 hours. The reaction is carried out by agitating the reaction mixture in a cylindrical reactor. In this manner, amphiphilic anisotropic powder having average particle size of 235 μm is obtained.

Preparation Example 4. Preparation of Hydrophilized Amphiphilic Anisotropic Powder First, 600 g of the aqueous dispersion of the anisotropic powder obtained as described above is mixed with 30 g of N-[3-(trimethoxysilyl)propyl]ethylenediamine) as a silane coupling agent and 60 g of ammonium hydroxide as a reaction modifier, and the reaction mixture is allowed to react at 25° C. for 24 hours to introduce a hydrophilic functional group. The reaction is carried out by agitating the reaction mixture in a cylindrical reactor to obtain hydrophilized amphiphilic anisotropic powder.

[Example and Comparative Example] Preparation of Emulsion Type Compositions

The oil-in-water type emulsion compositions of Example 1 and Comparative Examples 1 are prepared according to the compositions of the following Table 2.

Particularly, the oil phase ingredients are warmed to 70° C. and dissolved, the aqueous phase ingredients are warmed to 70° C. and dissolved, and the oil phase ingredients are added to the aqueous phase ingredients to carry out preliminary emulsification. Then, a thickener is added thereto to carry out secondary emulsification, followed by cooling and deaeration.

The ingredients used for the following Example and Comparative Example are shown below.
(a) Oil: Hydrogenated C6-C14 olefin polymer (Puresyn™, Exxon Mobil Chemical)
(b) Ceramide: Hydroxypropyl bislauramide monoethanolamine (MEA) (BP Ceramide PC-102, Macrocare Tech)
(c) Surfactant: Glyceryl stearate/PEG-50 stearate (Arlacel 170-PA-SG, Croda)
(d) Water-dispersed amphiphilic anisotropic powder: Solution obtained by dissolving 10 wt % of the amphiphilic anisotropic powder of Preparation Example 3 in 55 wt % of purified water and 35 wt % of butylene glycol
(e) Thickener: Xanthan gum (KELTROL CG SFT, TIC (THE INNOVATION COMPANY))
(f) Preservative: Phenoxyethanol (Clariant)
(e) Emollient: Ethylhexylglycerin (Sensiva SC50, Schilke & Mayr)
(h) Thickener; Water & Sorbitan isostearate & Polysorbate 20 & Polyisobutene & Polyacrylate-13 (SEPIPLUS 400, SEPPIC)
(f) Moisturizing agent: 1,3-Butylene glycol (Daicel)

TABLE 2

| (Unit: wt %) | Ex. 1 | Comp. Ex. 1 |
| --- | --- | --- |
| Hydrogenated C6-14 olefin polymer | 15 | 15 |
| Hydroxypropyl bislauramide monoethanolamine | 4 | 4 |
| Glyceryl stearate & PEG-50 stearate | 0 | 1 |
| Deionized water | To 100 | To 100 |
| Water-dispersed amphiphilic anisotropic powder | 10 | — |
| Xanthan gum | 0.05 | 0.05 |
| Phenoxyethanol | 0.3 | 0.3 |

TABLE 2-continued

| (Unit: wt %) | Ex. 1 | Comp. Ex. 1 |
| --- | --- | --- |
| Ethylhexyl glycerin | 0.05 | 0.05 |
| Water & Sorbitan isostearate & Polysorbate 20 & Polyisobutene/Polyacrylate-13 | 0.5 | 0.5 |
| 1,3-Butylene glycol | 4.5 | 8 |

[Test Example 1] Evaluation of Stability of Emulsion Particles

Each of the compositions according to Example 1 and Comparative Example 1 is allowed to stand at −15 to 60° C. for 4 weeks to determine the stability of emulsion particles. Example 1 maintains a stable emulsion state in a broad temperature range after the lapse of 4 weeks, and shows a dispersion state in which the ceramide particles and emulsion particles are dispersed homogeneously.

Each composition is photographed by an electron microscope at 30° C. right after it is prepared, and after it is allowed to stand at −15° C. for 4 weeks and returned to room temperature. The results are shown in FIG. 2 and FIG. 3.

Figure 2:
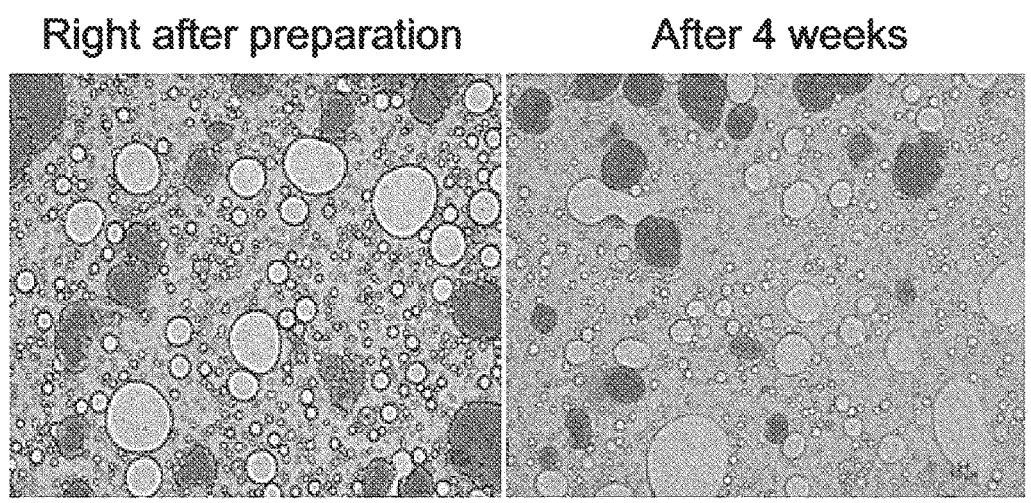
FIG. 2 shows the electron microscopic image (magnification: ×200) of the composition according to Example 1 right after it is prepared at room temperature, and after it is allowed to stand at −15° C. for 4 weeks and returned to room temperature.
Figure 3:
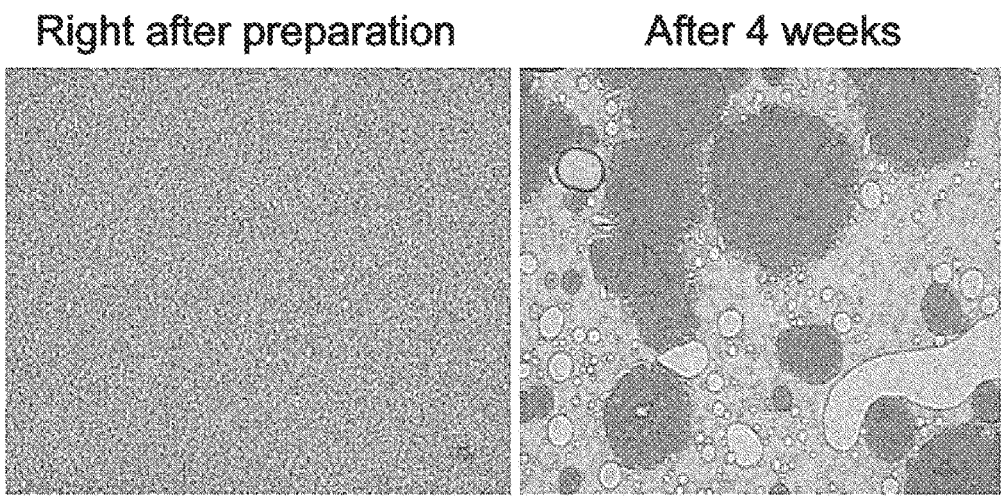
FIG. 3 shows the electron microscopic image (magnification: ×200) of the composition according to Comparative Example 1 right after it is prepared at room temperature, and after it is allowed to stand at −15° C. for 4 weeks and returned to room temperature.

It can be seen from the results of FIG. 2 and FIG. 3 that Example 1 includes emulsion particles and ceramide particles coexisting and dispersed homogeneously right after the preparation thereof. Even when Example 1 is allowed to stand under a severe condition for 4 weeks, it maintains a constant particle size without coalescence of particles and shows emulsion particles retained without a change in size. Thus, in the case of Example 1, the ceramide particles and emulsion particles are dispersed homogenously in the formulation. On the contrary, Comparative Example 1 using a conventional surfactant forms fine emulsion particles right after the preparation thereof, but causes precipitation of ceramide crystals after 4 weeks, shows coalescence of macrocrystals and undergoes an increase in size of emulsion particles due to coalescence of emulsion particles.

[Test Example 2] Evaluation of Change in Viscosity

Each of the compositions according to Example 1 and Comparative Example 1 is allowed to stand at −15° C. for 4 weeks and then returned to room temperature. Then, each composition is loaded on a black-colored rectangular plastic plate in an amount of about 1.5 g, and is allowed to stand at an angle of 45° C. to the ground surface for 15 minutes to observe the flowability of each composition. In this manner, each formulation is determined for a change in viscosity of the formulation.

Figure 4:
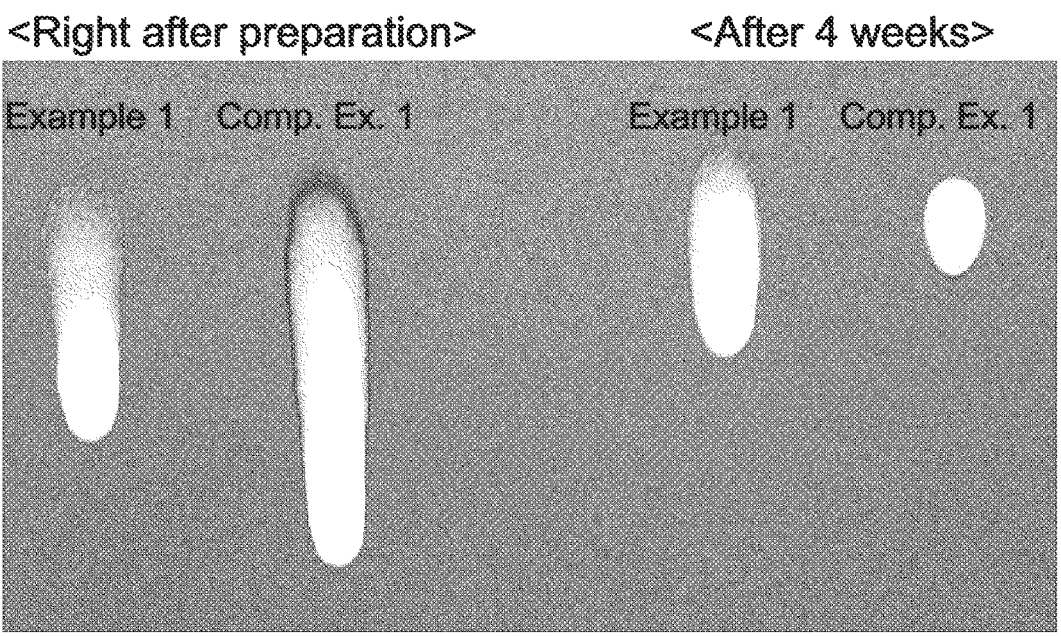
FIG. 4 is a photograph illustrating the flowability of each of the compositions according to Example 1 and Comparative Example 1 right after it is prepared at room temperature, and after it is allowed to stand at −15° C. for 4 weeks and returned to room temperature.

It can be seen from the results of FIG. 4 that Example 1 shows low-viscosity and good flowability both right after the preparation thereof and after 4 weeks under a severe condition, and thus forms a low-viscosity formulation causing little change in viscosity. On the contrary, Comparative Example 1 has low viscosity and high flowability right after the preparation thereof, but causes little dripping after 4 weeks. Thus, it can be seen that Comparative Example 1 undergoes a rapid increase in viscosity and is solidified.

The invention claimed is:
1. An oil-in-water emulsion cosmetic composition comprising amphiphilic anisotropic powder, an oil-phase ceramide contained in an oil phase, and ceramide particles contained in an aqueous phase, wherein the amphiphilic anisotropic powder comprises a first hydrophilic polymer spheroid and a second hydrophobic polymer spheroid, the first polymer spheroid and the second polymer spheroid are bound to each other with a structure in which one polymer spheroid at least partially penetrates into the other polymer spheroid, the first polymer spheroid has a core-shell structure, the shell has a functional group, and wherein the ceramide particles are formed as a crystalline phase in which a ceramide in the aqueous phase is surrounded with the amphiphilic anisotropic powder, and wherein the ceramide particles have an average particle diameter of 5-200 µm.

2. The composition according to claim 1, which comprises the ceramide in an amount of 0.5-10 wt % based on the total weight of the composition.

3. The composition according to claim 1, wherein the ceramide particles are present in an amount of 50-95 wt % based on the total weight of the ceramide.

4. The composition according to claim 1, which comprises the amphiphilic anisotropic powder in an amount of 0.1-30 wt % based on the total weight of the composition.

5. The composition according to claim 1, which has a viscosity of 1000-10000 cps.

6. The composition according to claim 1, wherein the ceramide is at least one selected from natural ceramides and pseudo-ceramides.

7. The composition according to claim 1, wherein the functional group is siloxane.

8. The composition according to claim 1, the second polymer spheroid and wherein the core of the first polymer spheroid comprise vinyl polymers, and the shell of the first polymer spheroid comprises a copolymer of a vinyl monomer with a functional group-containing monomer.

9. The composition according to claim 8, wherein the vinyl polymer is a vinyl aromatic polymer.

10. The composition according to claim 8, wherein the vinyl monomer is a vinyl aromatic monomer.

11. The composition according to claim 8, wherein the functional group-containing monomer is a siloxane-containing (meth)acrylate.

12. The composition according to claim 1, wherein the amphiphilic anisotropic powder has a symmetric shape, asymmetric snowman shape or asymmetric reverse snowman shape on the basis of the binding portion where the first polymer spheroid and the second polymer spheroid are bound to each other.

13. The composition according to claim 1, wherein the amphiphilic anisotropic powder has a particle size of 100-2500 nm.

14. The composition according to claim 1, wherein the amphiphilic anisotropic powder forms macroemulsion particles having an average particle diameter of 50-300 µm.

15. The composition according to claim 1, wherein the shell of the first polymer spheroid comprises a hydrophilic functional group introduced additionally thereto.

16. The composition according to claim 15, wherein the hydrophilic functional group is at least one selected from the group consisting of a carboxylate group, sulfone group, phosphate group, amino group, alkoxy group, ester group, acetate group, polyethylene glycol group and hydroxyl group.

17. The composition according to claim 1, wherein the shell of the first polymer spheroid comprises a saccharide-containing functional group additionally introduced thereto.

18. The composition according to claim 17, wherein the saccharide-containing functional group is derived from at least one selected from the group consisting of N-{N-(3-triethoxysilylpropyl) aminoethyl}gluconamide, N-(3-triethoxysilylpropyl) gluconamide and N- {N-(3 -triethoxysilylpropyl)aminoethyl}-oligo-hyaluronamide.

* * * * *